United States Patent [19]

Tomiyoshi et al.

[11] Patent Number: 5,137,917
[45] Date of Patent: Aug. 11, 1992

[54] SPERGUALIN-RELATED COMPOUND AND USE THEREOF

[75] Inventors: Tsugio Tomiyoshi; Takako Mae, both of Tokyo; Tetsushi Saino, Yono; Yoshihisa Umeda, Otsu, all of Japan

[73] Assignees: Nippon Kayaku Kabushiki Kaisha, Tokyo; Takara Shuzo Co., Ltd., Kyoto, both of Japan

[21] Appl. No.: 731,805

[22] Filed: Jul. 17, 1991

[30] Foreign Application Priority Data

Jul. 20, 1990 [JP] Japan .................................. 2-192443

[51] Int. Cl.$^5$ ............................................ A61K 31/195
[52] U.S. Cl. .................... 514/563; 514/558; 562/439; 562/560; 554/53
[58] Field of Search ............ 562/560, 439; 514/563, 514/558; 260/404.5

[56] References Cited

U.S. PATENT DOCUMENTS

| | | | |
|---|---|---|---|
| 4,430,346 | 2/1984 | Umezawa et al. | 424/311 |
| 4,518,532 | 5/1985 | Umezawa et al. | 260/404.5 |
| 4,529,549 | 7/1985 | Umezawa et al. | 260/404.5 |
| 4,556,735 | 12/1985 | Umezawa et al. | 564/157 |
| 4,851,446 | 7/1989 | Umezawa et al. | 514/620 |

FOREIGN PATENT DOCUMENTS

| | | |
|---|---|---|
| 0105193 | 4/1984 | European Pat. Off. . |
| 0241797 | 3/1987 | European Pat. Off. . |
| 0213526 | 10/1987 | European Pat. Off. . |
| 0309971 | 4/1989 | European Pat. Off. . |
| 0347820 | 12/1989 | European Pat. Off. . |

OTHER PUBLICATIONS

The Journal of Antibiotics, vol. XL, No. 9, pp. 1303-1315 and 1316-1324.
The Journal of Antibiotics, vol. XLI, No. 11, pp. 1629-1643.
Patent Abstracs of Japan, vol. 10, No. 31 (C-327) (2088), Feb. 6, 1986; & JP-A-60185758 (Biseibutsu Kagaku Kenkyukai).

Primary Examiner—Michael L. Shippen
Attorney, Agent, or Firm—Nields & Lemack

[57] ABSTRACT

Novel spergualin-related compounds represented by the general formula (I):

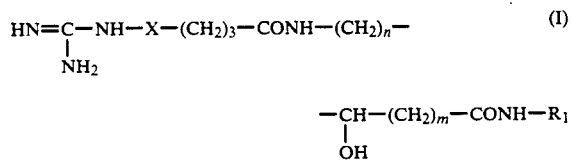

wherein X represents —$(CH_2)_{1-5}$— or a phenylene group which may be substituted; m represents 0, 1 or 2; n represents 1 or 2; and $R_1$ represents —$(CH_2)_{1-3}$—COOH, and pharmacologically acceptable salts thereof, possess an immunopotentiating activity, and are expected to be useful as immunopotentiators applicable to warm blooded animals.

9 Claims, No Drawings

SPERGUALIN-RELATED COMPOUND AND USE THEREOF

BACKGROUND OF THE INVENTION

1. Field of the Invention

The present invention relates to a novel spergualin-related compound which is useful for an immunopotentiator and which has a high specificity, and to medical use of the compound.

2. Related Art Statement

Spergualin is a compound having an anti-tumor activity and immunosuppressive activity which is obtained from the culture broth of Bacillus laterosporus (U.S. Pat. No. 4,416,899) and many derivatives of spergualin have been synthesized (cf., U.S. Pat. No. 4,430,346, U.S. Pat. No. 4,518,532, U.S. Pat. No. 4,529,549, U.S. Pat. No. 4,556,735, U.S. Pat. No. 4,851,446, EP-A-213526, EP-A-241,797). These compounds are expected to be drugs as carcinostatic agents or immunosuppresants.

Currently, some immunopotentiators have been developed but new immunopotentiators having a higher specificity have still been desired.

SUMMARY OF THE INVENTION

Therefore, an object of the present invention is to provide a novel compound useful as an immunopotentiator.

Another object of the present invention is to provide a pharmaceutical composition comprising the novel compound as an active ingredient, which is particularly useful for an immunopotentiator.

A further object of the present invention is to provide a method for immunopotentiation which comprises administering the novel compound to a warm-blooded animal.

A still further object of the present invention is to provide use of the novel compound as an immunopotentiator.

A first aspect of the present invention relates to a novel spergualin derivative represented by the general formula (I):

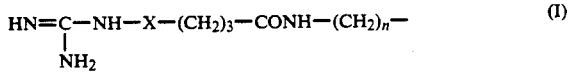

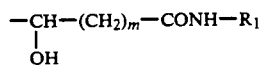

wherein X represents $-(CH_2)_{1-5}-$ or a phenylene group which may be substituted; m represents 0, 1 or 2; n represents 1 or 2; and $R_1$ represents $-(CH_2)_{1-3}-COOH$; and a pharmacologically acceptable salt thereof.

A second aspect of the present invention relates to a pharmaceutical composition for immunopotentiation comprising as an active ingredient the novel spergualin derivative represented by the general formula (I) or the pharmaceutically acceptable salts thereof, together with a pharmaceutically carrier.

A third aspect of the present invention relates to a method for immunopotentiation which comprises administering an effective amount of the novel spergualin derivative represented by the general formula (I) or the pharmaceutically acceptable salt thereof to a warm-blooded animal having a reduced immunity.

A fourth aspect of the present invention relates to use of the novel spergualin derivative represented by the general formula (I) or the pharmaceutically acceptable salt thereof for the production of a pharmaceutical composition for immunopotentiation.

DETAILED DESCRIPTION OF THE PREFERRED EMBODIMENTS

The novel spergualin derivatives are represented by the general formula (I):

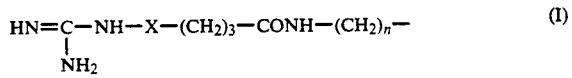

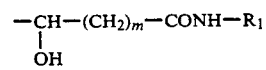

wherein X represents $-(CH_2)_{1-5}-$ or a phenylene group which may be substituted; m represents 0, 1 or 2; n represents 1 or 2; and $R_1$ represents $-(CH_2)_{1-3}-COOH$.

The phenylene group of X may be substituted with a halogen atom such as chlorine, fluorine and bromine atom; a lower alkyl group such as methyl, ethyl, propyl, t-butyl and pentyl group; or a lower alkoxy group such as methoxy, ethoxy, propoxy, t-butoxy and pentoxy group. X is preferably $-(CH_2)_3$ or $-(CH_2)_5-$, more preferably $-(CH_2)_3-$. m is preferably 0 or 1. n is preferably 1. $R_1$ is preferably $-(CH_2)_2-COOH$ or $-(CH_2)_3-COOH$.

The compounds represented by the general formula (I) may form salts with acids. As the acids for forming the salts, any of inorganic acids and organic acids may be used as long as they are non-toxic. As the inorganic acids, there are no particular limitation but hydrochloric acid, sulfuric acid, nitric acid and phosphoric acid are preferred. As the organic acids, there are no particular limitation but preferred are acetic acid, propionic acid, succinic acid, fumaric acid, maleic acid, malic acid, tartaric acid, glutaric acid, citric acid, benzenesulfonic acid, toluenesulfonic acid, methanesulfonic acid, ethanesulfonic acid, propanesulfonic acid, aspartic acid, and glutamic acid.

In the spergualin derivative of the general formula (I) of the present invention, steric configuration of the carbon atom to which the hydroxy group is bound indicates S, R or RS form. In particular, S or RS form are preferable. The representative compounds in the present invention are listed in the following Table 1.

TABLE 1

$$HN=C-NH-X-(CH_2)_3-CONH-(CH_2)_n-\overset{*}{C}H-(CH_2)_m-CONH-R_1 \quad (I)$$
$$\underset{NH_2}{|} \qquad \qquad \underset{OH}{|}$$

| Compound No. | X | n | m | Steric Configuration of C* | R₁ |
|---|---|---|---|---|---|
| 1 | —(CH₂)₃— | 1 | 1 | S, R or RS | —CH₂—COOH |
| 2 | —(CH₂)₃— | 1 | 1 | S, R or RS | —(CH₂)₂—COOH |
| 3 | —(CH₂)₃— | 1 | 1 | S, R or RS | —(CH₂)₃—COOH |
| 4 | —CH₂— | 1 | 1 | S, R or RS | —CH₂—COOH |
| 5 | —CH₂— | 1 | 1 | S, R or RS | —(CH₂)₂—COOH |
| 6 | —CH₂— | 1 | 1 | S, R or RS | —(CH₂)₃—COOH |
| 7 | —(CH₂)₂— | 1 | 1 | S, R or RS | —CH₂—COOH |
| 8 | —(CH₂)₂— | 1 | 1 | S, R or RS | —(CH₂)₂—COOH |
| 9 | —(CH₂)₂— | 1 | 1 | S, R or RS | —(CH₂)₃—COOH |
| 10 | —(CH₂)₄— | 1 | 1 | S, R or RS | —CH₂—COOH |
| 11 | —(CH₂)₄— | 1 | 1 | S, R or RS | —(CH₂)₂—COOH |
| 12 | —(CH₂)₄— | 1 | 1 | S, R or RS | —(CH₂)₃—COOH |
| 13 | —(CH₂)₅— | 1 | 1 | S, R or RS | —CH₂—COOH |
| 14 | —(CH₂)₅— | 1 | 1 | S, R or RS | —(CH₂)₂—COOH |
| 15 | —(CH₂)₅— | 1 | 1 | S, R or RS | —(CH₂)₃—COOH |
| 16 |  | 1 | 1 | S, R or RS | —CH₂—COOH |
| 17 |  | 1 | 1 | S, R or RS | —(CH₂)₂—COOH |
| 18 |  | 1 | 1 | S, R or RS | —(CH₂)₃—COOH |
| 19 | —(CH₂)₂— | 1 | 0 | S, R or RS | —CH₂—COOH |
| 20 | —(CH₂)₂— | 1 | 0 | S, R or RS | —(CH₂)₂—COOH |
| 21 | —(CH₂)₂— | 1 | 0 | S, R or RS | —(CH₂)₃—COOH |
| 22 | —(CH₂)₃— | 1 | 0 | S, R or RS | —CH₂—COOH |
| 23 | —(CH₂)₃— | 1 | 0 | S, R or RS | —(CH₂)₂—COOH |
| 24 | —(CH₂)₃— | 1 | 0 | S, R or RS | —(CH₂)₃—COOH |
| 25 | —(CH₂)₄— | 1 | 0 | S, R or RS | —CH₂—COOH |
| 26 | —(CH₂)₄— | 1 | 0 | S, R or RS | —(CH₂)₂—COOH |
| 27 | —(CH₂)₄— | 1 | 0 | S, R or RS | —(CH₂)₃—COOH |
| 28 | —(CH₂)₅— | 1 | 0 | S, R or RS | —CH₂—COOH |
| 29 | —(CH₂)₅— | 1 | 0 | S, R or RS | —(CH₂)₂—COOH |
| 30 | —(CH₂)₅— | 1 | 0 | S, R or RS | —(CH₂)₃—COOH |
| 31 |  | 1 | 0 | S, R or RS | —CH₂—COOH |
| 32 |  | 1 | 0 | S, R or RS | —(CH₂)₂—COOH |
| 33 |  | 1 | 0 | S, R or RS | —(CH₂)₃—COOH |
| 34 | —(CH₂)₃— | 2 | 0 | S, R or RS | —CH₂—COOH |
| 35 | —(CH₂)₃— | 2 | 0 | S, R or RS | —(CH₂)₂—COOH |
| 36 | —(CH₂)₃— | 2 | 0 | S, R or RS | —(CH₂)₃—COOH |
| 37 |  | 2 | 0 | S, R or RS | —CH₂—COOH |

TABLE 1-continued $$HN=C-NH-X-(CH_2)_3-CONH-(CH_2)_n-\overset{*}{C}H-(CH_2)_m-CONH-R_1 \quad (I)$$
$$\overset{|}{NH_2} \qquad\qquad\qquad\qquad\qquad \overset{|}{OH}$$

| Compound No. | X | n | m | Steric Configuration of C* | $R_1$ |
|---|---|---|---|---|---|
| 38 | 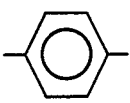 | 2 | 0 | S, R or RS | $-(CH_2)_2-COOH$ |
| 39 | 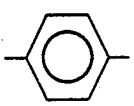 | 2 | 0 | S, R or RS | $-(CH_2)_3-COOH$ |

Among the compounds listed in Table 1, the following compound is the most preferable compound. The compound No. 2

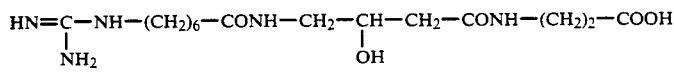

The steric configuration of the asymmetric carbon atom in Compound No. 2 is preferably S form.

The compounds listed above are all novel and may be prepared by the following process. That is, the compounds are obtained by removing a protective group from compounds represented by the formula (II):

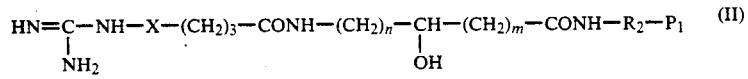

wherein X, m and n are as defined above; $R_2$ represents $-(CH_2)_{1-3}-COO-$; and $P_1$ represents a protective group of the carboxy group.

The protected compounds of the general formula (II) which are the starting compounds of the present invention may be synthesized by the following method.

Protected amino acids represented by the formula (III):

wherein $R_2$ and $P_1$ are as defined above; are reacted with reactive derivatives of protected amino acids represented by the formula (IV):

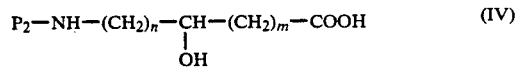

wherein $P_2$ represents a protective group of the amino group which is different from $P_1$; and n and m are as defined above. Then the amino protective group $P_2$ is removed and reacted with reactive derivatives of ω-guanidino-fatty acids represented by the formula (V):

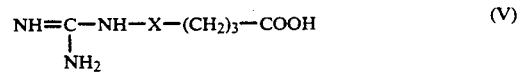

wherein X is as defined above. Thus, the compounds represented by the formula (II) are obtained.

The condensation reaction as described above may be carried out by methods generally used in peptide chemistry. Examples of these methods include a carbodiimide method using dicyclohexylcarbodiimide, 1-ethyl-3-(3'-dimethylaminopropyl)-carbodiimide or the like; a mixed acid anhydride method using ethyl chlorocarbonate, isobutyl chlorocarbonate or the like; an activated ester method using a cyanomethyl ester, a vinyl ester, a substituted or unsubstituted phenyl ester, a thiophenyl ester or a hydroxysuccinimide ester or the like; an O-acylhydroxylamine derivative method using acetoxime, cyclohexanone oxime or the like; an N-acyl compound method using carbonyldiimidazole; and a carboxylic acid activation method using 1,3- thiazolidine-2-thione or the like.

As a solvent for the condensation reaction, any solvent applied to conventional peptide bond-forming reactions may be used. Examples of such a solvent include ethers such as diethyl ether, tetrahydrofuran and dioxan; esters such as ethyl acetate; ketones such as acetone and methyl ethyl ketone; halogenated hydrocarbons such as methylene chloride and chloroform; amides such as dimethylformamide and dimethylacetamide; nitriles such as acetonitrile. These solvents may be used singly or in combination thereof. Where the solvent is miscible with water, the solvent may be used as an admixture with water.

As the protective group which may be used in the present invention, there are a lower alkyl group, t-butyl group, benzyl group, a substituted benzyl group, and the like.

The protective group in the compounds shown by the general formula (II) may be split off by reactions such as reduction, hydrolysis and acid decomposition. Such reactions are carried out generally in a solvent at −60° C. to the boiling point of a solvent, preferably at −50° to 100° C. Examples of the solvent used include water and hydrophilic organic solvents, for example, a lower alcohol such as methanol and ethanol; a ketone such as acetone and methyl ethyl ketone; an amide such as dimethylformamide and dimethylacetamide; a cyclic ether such as tetrahydrofuran and dioxane; a lower fatty acid such as acetic acid and trifluoroacetic acid; liquid ammonia; and liquid hydrogen fluoride. These solvents may be appropriately used.

The compounds of general formula (I) may be isolated from the reaction solution of the compounds from which the protective group has been split off, by conventional methods for purification, for example, where the protective group is removed by catalytic reduction using palladium black, the filtrate obtained by filtering the catalyst off is concentrated under reduced pressure and the residue is purified by known method using chromatography using CM-Sephadex ® (Na+) or Sephadex ® LH-20. Where the protective group is removed with trifluoroacetic acid, the reaction solution is also concentrated under reduced pressure and the residue is purified by the method described above. Thus, the desired compounds may be purified.

By the purification method described above, the compounds of the general formula (I) may be obtained in the form of hydrochloride. The salt may also be converted into other salts. For example, the hydrochloride is dissolved in water and the resulting aqueous solution is passed through a strongly basic ion exchange resin. The non-adsorbed fraction containing the compounds of general formula (I) is collected and a desired acid is added thereto for neutralization. The mixture is then evaporated to dryness under reduced pressure. In this case, water, or, if necessary, a hydrophilic organic solvent such as methanol, ethanol, acetone, tetrahydrofuran, dioxan, or the like is added. When the organic solvent is contained, the solvent is distilled off under reduced pressure and freeze-dried to give the desired salts. The desired salts may also be obtained by adding an aqueous solution of silver hydroxide to the hydrochloride of the compounds of the general formula (I) to neutralize hydrochloric acid, filtering insoluble silver chloride, adding a desired acid to the filtrate to form the salts, and freeze-drying.

The physiological activity of the compounds of the present invention is demonstrated by the following experiments wherein the effects of potentiating antibody production were determined.

EXPERIMENT 1

1. Method

Sheep red blood cells (SRBC) were intravenously injected to CDF$_1$-SLC mice (5 mice in each group) in a dose of $1 \times 10^8/0.2$ ml for booster. The compound of the present invention was diluted with physiological saline in various concentrations. Each diluted solution was administered once in a daily dose of 0.1 ml per 10 g of body weight (0.1 ml/10 g/day) for consecutive 3 days from the next day after sensitization. Mice were sacrificed 4 days after the sensitization. The count of anti-SRBC antibody-producing cells (plaque forming cell, PFC) in the spleen cells was determined and the PFC count was calculated per $10^6$ of the spleen cells. As is shown in the following equation, the effect of the compound of the present invention is expressed by a potentiation rate (%) of the PFC count in the group administered with the compound of the present invention, as compared to the PFC count in the control group.

$$\text{Potentiation rate (\%)} = \left( \frac{\text{PFC count in the administered group}}{\text{PFC count in the control group}} \right) \times 100$$

2. Results

The effects of representative examples of the compounds of the present invention on potentiating antibody production is shown in Table 2.

TABLE 2

| Effects of Compounds of This Invention on Potentiating Antibody Production | | |
|---|---|---|
| Compound No. | Effect of Potentiating Antibody Production (control: 100%) Dose | |
| | 3 mg/kg | 3 mg/kg |
| 2* | 127 | 151 |
| 3* | 128 | 128 |
| 5* | 93 | 127 |
| 14* | 84 | 113 |
| 21* | 152 | 173 |
| 24* | 169 | 166 |
| Control: | | |
| Physiological saline | 100 | 100 |

*RS form

EXPERIMENT 2

1. Method

Methylprednisolone was intraperitoneally administered to BALB/C mice (female, age of 8 weeks, Japan Kurea) in a dose of 400 mg/kg for 9 days to prepare immunosuppressed mice. On Day 6, the mice was boosted by intravenous injection of sheep red blood cells (SRBC, Japan Biological Material Center) in a dose of $1 \times 10^6$ cells. On Day 6 after the sensitization the count of antibody-producing cells (plaque forming cell, PFC) in the spleen cells was determined. A test compound was intravenously administered in each dose shown in Table 3 only on the next day after the sensitization.

In the same way as in Experiment 1, a potentiation rate of PFC count was determined.

The tested compounds were as follows:

Compound No. 2 (RS form)

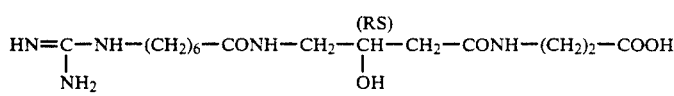

Compound No. 2 (S form)

-continued

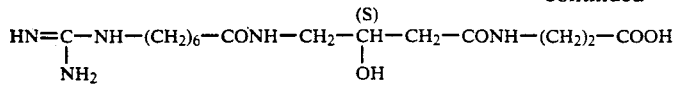

2. Results

The effects of the tested compounds on potentiating antibody production are shown in Table 3.

TABLE 3

| | Potentiation Rate of PFC Count | |
|---|---|---|
| Treatment | vs. Normal (%) | vs. Methyl-prednisolone (%) |
| Experiment 2-1 | | |
| Normal | 100 | |
| Methylprednisolone | 37.5 | 100 |
| Compound No. 2 (RS form) | | |
| 10 mg/kg | 65.6 | 174.8 |
| 30 mg/kg | 96.0 | 255.8 |
| Experiment 2-2 | | |
| Normal | 100 | |
| Methylprednisolone | 77.2 | 100 |
| Compound No. 2 (S form) | | |
| 30 mg/kg | 163.5 | 211.8 |

As is evident from the foregoing experimental results, the compounds of the present invention possess an excellent immunopotentiating activity and are expected as immunopotentiators and other drugs.

Where the compounds of the present invention are used as drugs, the compounds are formulated into pharmaceutical preparations in a conventional manner, if necessary, together with additives used for pharmaceutical preparations. The preparations may be administered orally or parenterally. The additives such as excipients or carriers may be chosen from those pharmacologically acceptable. The kind and composition of excipients or carriers to be chosen may vary depending on route or method for administration. As liquid carriers, there may be used, for example, water, an alcohol, animal and vegetable oil such as soybean oil, olive oil and mineral oil; or synthetic oil. As solid carriers, there may be used sugars such as maltose and sucrose; amino acids; cellulose derivatives such as hydroxypropyl cellulose; or organic acid salts such as magnesium stearate.

In the case of injection, it is desired to use, as a dissolution liquid, physiological saline, various buffer solutions, a solution of sugar such as glucose, inositol, mannitol and lactose, or a glycol such as ethylene glycol and polyethylene glycol. Alternatively, a sugar such as inositol, mannitol and lactose, or an amino acid such as phenylalanine may be used as the carriers to prepare a freeze-dried preparation. Upon administration, such a preparation may be dissolved in a solvent suitable for injection such as liquid for intravenous administration, e.g., sterile water, physiological saline, a glucose solution, an electrolyte solution or an amino acid solution, and the resulting solution may be administered.

A content of the compound of the present invention in the pharmaceutical preparation may vary depending upon the mode of preparation but is generally in a range of 0.1 to 100 wt %, preferably 1 to 98 wt %. In the case of, e.g., injection, it is desired to contain the active ingredient generally in a range of 0.1 to 30 wt %, preferably 1 to 10 wt %.

Where it is desired to immunopotentiate a warm blooded animal (including human being) using the compound of the general formula (I), an effective dose of the compound of the general formula (I) may be administered to the warm blooded animal, whereby antibody production is potentiated and immunity is activated.

Where the compound of the general formula (I) is orally administered, the compound is used in the form of a tablet, a capsule, a powder, a granule, a solution or a dry syrup, generally together with solid carriers or liquid carriers as described above. The capsule, granule and powder contain generally 5 to 100 wt %, preferably 25 to 98 wt % of the active ingredient.

Dose may be determined depending upon age, body weight and condition of patient to be administered and therapeutic purpose but is generally 1–500 mg/kg/day, that is, 1–100 mg/kg/day in parenteral administration and 5 to 500 mg/kg/day in oral administration.

PREPARATION EXAMPLE 1

Distilled water for injection is added to 30 parts by weight of the hydrochloride of Compound No. 2 shown in Table 1 to make the whole volume 2000 parts. After dissolving the hydrochloride of Compound 2, the solution is subjected to cell-free filtration using Millipore Filter GS type. The filtrate (2 g) is taken up in a vial bottle of 10 ml volume and freeze-dried to give a freeze-dried injection containing 30 mg of the hydrochloride of Compound No. 2 per vial.

PREPARATION EXAMPLE 2

50 parts by weight of the hydrochloride of Compound No. 21 shown in Table 1, 600 parts of lactose, 330 parts of crystalline cellulose and 20 parts of hydroxypropyl cellulose are thoroughly kneaded with each other and the mixture is compressed using a roller compacter. By grinding and sieving through a mesh of 16 to 60 mesh, granules are obtained.

Next, the present invention is described more specifically with reference to the examples below but is not deemed to be limited thereto.

EXAMPLE 1

Synthesis of 16-guanidino-7-(RS)-hydroxy-5,10-dioxo-4,9-diazahexadecanoic acid (Compound No. 2)

a) Synthesis of benzyl 9-t-butyloxycarbonyl-7-(RS)-hydroxy-5-oxo-4,9-diazanonanoate In 60 ml of dichloromethane were dissolved 2.5 g (11.40 mmols) of γ-N-t-butyloxycarbonyl-β-(RS)-hydroxybutanoic acid and 2.6 g (17.10 mmols) of N-hydroxybenzotriazole. The solution was cooled with ice and 3.5 g (17.10 mmols) of N,N'-dicyclohexylcarbodiimide was added to the solution. The mixture was reacted for 15 minutes under ice cooling. Then, a solution of 4.0 g (11.40 mmols) of β-alanine benzyl ester p-toluenesulfonic acid salt and 1.3 g (12.54 mmols) of triethylamine in dichloromethane was added to the solution under ice cooling. The temperature was then reverted to room temperature and the reaction was carried out for several hours. Insoluble matters were filtered off and the filtrate was concentrated under reduced pressure. The oily residue was dissolved in 150 ml of ethyl acetate followed by washing sequentially with distilled water, 5% phosphoric acid, 5% sodium carbonate aqueous solution and then saturated sodium chloride aqueous solution. The organic layer was dried over anhydrous sodium sulfate. The supernatant was concentrated under reduced pressure to give 5.1 g of light yellow oily product. The oily product was subjected to column chromatography using Silica Gel 60 (manufactured by Merck Inc.) and development was performed with a solvent mixture of chloroform-methanol (30:1, v/v) to give 3.5 g (yield, 80.83%) of the oily product.

NMR (CD$_3$OD)

$\delta = 1.47$ (s, 9H), 2.1–2.5 (d, 2H, J=6 Hz), 2.4–2.8 (t, 2H, J=6 Hz), 2.9–3.3 (d, 2H, J=6 Hz), 3.2–3.7 (t, 2H, J=6 Hz), 3.8–4.3 (q, H, J=6 Hz), 5.15 (s, 2H), 7.37 (s, 5H)

TLC (chloroform:methanol = 10:1, v/v)

Rf=0.4 b) Synthesis of benzyl 8-amino-7-(RS)-hydroxy-5-oxo-4-azaoctanoate hydrochloride After 3.5 g (9.20 mmols) of benzyl 9-t-butyl-oxycarbonyl-7-(RS)-hydroxy-5-oxo-4,9-diazanonanoate was dissolved in 10 ml of dichloromethane, 10 ml of 4N hydrochloric acid-dioxan solution was added to the solution under ice cooling. The temperature was reverted to room temperature and the mixture was reacted for 3 hours. The reaction solution was concentrated under reduced pressure. The resulting white residue was subjected to decantation with n-hexane and ether. Concentration under reduced pressure gave 2.9 g (yield, 100%) of white crystals.

TLC (chloroform:methanol:17% ammonia water=6:2.5:0.5, v/v)

Rf=0.35 c) Synthesis of benzyl 16-guanidino-7-(RS)-hydroxy-5,10-dioxo-4,9-diazahexadecanoate hydrochloride After 2.47 g (11.04 mmols) of 7-guanidinoheptanoic acid was dissolved in 40 ml of dimethylformamide, 1.53 g (13.25 mmols) of N-hydroxysuccinimide and 2.73 g (13.25 mmols) of N,N'-dicylohexylcarbodiimide were added to the solution under ice cooling. The mixture was reacted at room temperature overnight. The precipitates were filtered off and the filtrate was used for the subsequent reaction as it was.

After 2.9 g (9.20 mmols) of white crystalline benzyl 8-amino-7-(RS)-hydroxy-5-oxo-4-azaoctanoate hydrochloride was dissolved in 40 ml of dimethylformamide, 1.02 g (10.12 mmols) of triethylamine was added to the solution under ice cooling. Then the aforesaid solution of 7-guanidinoheptanoate hydrochloride N-hydroxysuccinimide ester in dimethylformamide was added to the mixture followed by reacting at room temperature overnight. The reaction solution was filtered and the filtrate was concentrated under reduced pressure. After decantation of the resulting oily residue twice with 100 ml of n-hexane, the system was concentrated under reduced pressure. The resulting oily product was subjected to column chromatography using Silica Gel 60 (manufactured by Merck Inc.) and development was performed with a solvent mixture of chloroform-methanol17% ammonia water (6:2.5 :0.5, v/v) to give 4.1 g (yield, 91.72%) of the oily product.

NMR (CD$_3$OD)

$\delta = 0.9–2.1$ (m, 8H), 2.1–3.0 (m, 6H), 3.0–3.9 (m, 6H), 3.9–4.4 (m, H), 5.23 (s, 2H), 7.46 (s, 5H)

IR (KBr)

$\nu$ (cm$^{-1}$)=3300, 2940, 2600, 2500, 1730, 1650, 1540, 1170

TLC (chloroform:methanol:17% ammonia water=6:2.5:0.5, v/v)

Rf=0.34 d) Synthesis of 16-guanidino-7-(RS)-hydroxy-5,10-dioxo-4,9-diazahexadecanoic acid After 4.1 g (8.43 mmols) of benzyl 16-guanidino-7-(RS)-hydroxy-5,10-dioxo-4,9-diazahexadecanoate was dissolved in 40 ml of methanol, 10 ml of acetic acid and 0.4 g of palladium black were added to the solution followed by catalytic reduction at 50° C. for 4 hours under normal pressure. The catalyst was filtered off and the filtrate was concentrated under reduced pressure to give 5.0 g of the oily product. This oily product was dissolved in 60 ml of distilled water and the solution was passed through a column packed with 500 ml of CM-Sephadex ® C-25 (Na+). After eluting with distilled water, the fraction containing the desired product was collected and evaporated to dryness under reduced pressure to give 3.5 g of the dry solid. In order to remove a small amount of impurities, the resulting dry solid was dissolved in 40 ml of distilled water and the solution was passed through a column packed with 300 ml of HP-20 ® manufactured by Mitsubishi Chemical Industry Co., Ltd. By eluting with distilled water, the fraction containing the desired product was collected and concentrated under reduced pressure. The resulting oily product was dissolved in 20 ml of distilled water. Insoluble matters were filtered off and the filtrate was freeze-dried to give 1.34 g (yield, 44.42%) of the desired product.

NMR (D$_2$O, external TMS)

$\delta = 1.5–2.5$ (m, 8H), 2.5–3.2 (m, 6H), 3.4–4.1 (m, 6H), 4.3–4.8 (m, H)

IR (KBr)

$\nu$(cm$^{-1}$)=3320, 2940, 1635, 1550, 1410, 1185, 1095

As is described in the followings, the various desired compounds represented by the general formula (I) were obtained in a manner similar to the procedures in d) in the example described above, using the corresponding compounds represented by the general formula (II). The compounds represented by the general formula (II) can be obtained by forming peptide bond, in sequence, in a conventional manner, in a manner similar to the procedures of a) to c) in the example described above, using the corresponding amino acids.

SYNTHESIS OF COMPOUND NO. 1 i) Benzyl 15-guanidino-6-(RS)-hydroxy-4,9-dioxo-3,8-diazapentadecanoate hydrochloride (Corresponding Compound of formula (II))

NMR (CD$_3$OD)

$\delta = 0.9–2.0$ (m, 8H), 2.0–2.7 (m, 4H), 2.8–3.5 (m, 4H), 3.8–4.4 (m, H), 4.0 (s, 2H), 5.1 (s, 2H), 7.37 (s, 5H)

IR (KBr)

$\nu$ (cm$^{-1}$)=3330, 2940, 1745, 1650, 1545, 1195, 1090, 1030

TLC (chloroform:methanol = 17% ammonia water=6:2.5:0.5, v/v)

Rf=0.28 ii)
15-Guanidino-6-(RS)-hydroxy-4,9-dioxo-3,8-diazapentadecanoic acid (Compound No. 1)

NMR (D$_2$O, external TMS)

$\delta$ = 1.5–2.5 (m, 8H), 2.5–3.3 (m, 4H), 3.4–4.0 (m, 4H), 4.3–4.9 (m, H), 4.47 (s, 2H)

IR (KBr)

$\delta$ (cm$^{-1}$) = 3340, 2930, 1640, 1540, 1410, 1230

SYNTHESIS OF COMPOUND NO. 3 i) Benzyl 17-guanidino-8-(RS)-hydroxy-6,11-dioxo-5,10-diazaheptadecanoate hydrochloride (Corresponding Compound of formula (II))

NMR (CD$_3$OD)

$\delta$ = 0.9–2.0 (m, 10H), 2.0–2.7 (m, 6H), 2.8–3.5 (m, 6H), 3.8–4.2 (m, H), 5.07 (s, 2H), 7.28 (s, 5H)

IR (KBr)

$\nu$ (cm$^{-1}$) = 3300, 2940, 2360, 1735, 1640, 1460, 1165, 1090

TLC (chloroform:methanol:17% ammonia water = 6:2.5:0.5, v/v)

Rf = 0.63 ii)
17-Guanidino-8-hydroxy-6,11-dioxo-5,10-diazaheptadecanoic acid (Compound No. 3)

NMR (D$_2$O, external TMS)

$\delta$ = 1.5–2.5 (m, 10H), 2.5–3.1 (m, 6H), 3.3–4.0 (m, 6H), 4.2–4.8 (m, H)

IR (KBr)

$\nu$ (cm$^{-1}$) = 3320, 3150, 2930, 2860, 1670, 1640, 1540, 1400, 1305, 1110

SYNTHESIS OF COMPOUND NO. 5 i) Benzyl 14-guanidino-7-(RS)-hydroxy-5,10-dioxo-4,9-diazatetradecanoate hydrochloride (Corresponding Compound of formula (II))

NMR (CD$_3$OD, external TMS)

$\delta$ = 1.5–2.1 (m, 4H), 2.2–3.6 (m, 6H), 3.1–3.9 (m, 6H), 3.9–4.5 (m, H), 5.26 (s, 2H), 7.48 (s, 5H)

IR (KBr)

$\nu$ (cm$^{-1}$) = 3300, 3180, 1730, 1650, 1540, 1435, 1400, 1250, 1170, 1075

TLC (chloroform:methanol:17% ammonia water = 6:2.5:0.5, v/v)

Rf = 0.48 ii)
14-Guanidino-7-(RS)-hydroxy-5,10-dioxo-4,9-diazatetradecanoic acid (Compound No. 5)

NMR (D$_2$O, external TMS)

$\delta$ = 1.7–2.5 (m, 4H), 2.6–3.4 (m, 6H), 3.4–4.2 (m, 6H), 4.3–4.9 (m, H)

IR (KBr)

$\nu$ (cm$^{-1}$) = 3340, 3260, 1720, 1645, 1555, 1540, 1445, 1410, 1250, 1185

SYNTHESIS OF COMPOUND NO. 8 i) Benzyl 15-guanidino-7-(RS)-hydroxy-5,10-dioxo-4,9-diaza-pentadecanoate hydrochloride (Corresponding Compound of formula (II))

NMR (CD$_3$OD, external TMS)

$\delta$ = 1.4–2.1 (m, 6H), 2.1–3.0 (m, 6H), 3.2–3.9 (m, 6H), 4.0–4.5 (m, H), 5.28 (s, 2H), 7.50 (s, 5H)

IR (KBr)

$\nu$ (cm$^{-1}$) = 3310, 3180, 2940, 1730, 1645, 1540, 1400, 1170

TLC (chloroform:methanol:17% ammonia water = 6:2.5:0.5, v/v)

Rf = 0.48 ii)
15-Guanidino-7-(RS)-hydroxy-5,10-dioxo-4,9-diazapentadecanoic acid (Compound No. 8)

NMR (D$_2$O, external TMS)

$\delta$ = 1.6–2.5 (m, 6H), 2.6–3.5 (m, 6H), 3.6–4.4 (m, 6H), 4.5–5.1 (m, H)

IR (KBr)

$\nu$ (cm$^{-1}$) = 3330, 2940, 1645, 1540, 1415, 1360, 1180, 1075

SYNTHESIS OF COMPOUND NO. 14 i) Benzyl 18-guanidino-7-(RS)-hydroxy-5,10-dioxo-4,9-diazaoctadecanoate hydrochloride (Corresponding Compound of formula (II))

NMR (CD$_3$OD, external TMS)

$\delta$ = 1.1–2.0 (m, 12H), 2.1–3.0 (m, 6H), 3.0–3.8 (m, 6H), 3.8–4.4 (m, H), 5.20 (s, 2H), 7.38 (s, 5H)

IR (KBr)

$\nu$ (cm$^{-1}$) = 3310, 2930, 2860, 2330, 1730, 1635, 1460, 1170

TLC (chloroform:methanol:17% ammonia water = 6:2.5:0.5, v/v)

Rf = 0.48 ii)
18-Guanidino-7-(RS)-hydroxy-5,10-dioxo-4,9-diazaoctadecanoic acid (Compound No. 14)

NMR (D$_2$O, external TMS)

$\delta$ = 1.5–2.6 (m, 12H), 2.7–3.6 (m, 6H), 3.7–4.5 (m, 6H), 4.6–5.2 (m, H)

IR (KBr)

$\nu$ (cm$^{-1}$) = 3300, 3160, 2920, 2850, 1720, 1640, 1555, 1410, 1375, 1350, 1180, 1095

SYNTHESIS OF COMPOUND NO. 21 i) Benzyl 15-guanidino-7-(RS)-hydroxy-6,10-dioxo-5,9-diazapentadecanoate hydrochloride (Corresponding Compound of formula (II))

NMR (CD$_3$OD, external TMS)

$\delta$ = 1.1–2.9 (m, 12H), 3.1–3.9 (m, 6H), 4.1–4.5 (t, H, J = 6 Hz), 5.27 (s, 2H), 7.47 (s, 5H)

IR (KBr)

$\nu$ (cm$^{-1}$) = 3310, 2940, 1725, 1645, 1540, 1450, 1255, 1165, 1110

TLC (chloroform:methanol:17% ammonia water = 6:2.5:0.5, v/v)

Rf = 0.3 ii)

15-Guanidino-7-(RS)-hydroxy-6,10-dioxo-5,9-diazapentadecanoic acid (Compound No. 21)

NMR (D$_2$O, external TMS) δ=1.5-2.5 (m, 8H), 2.5-3.1 (m, 4H), 3.4-4.2 (m, 6H), 4.5-4.9 (t, H, J=5 Hz)

IR (KBr)

ν (cm$^{-1}$)=3320, 2940, 1710, 1645, 1540, 1435, 1240, 1170, 1110

SYNTHESIS OF COMPOUND NO. 24 i) Benzyl 16-guanidino-7diazahexadecanoate RS)-hydroxy-6,10-dioxo-5,9-diazahexadecanoate hydrochloride (Corresponding Compound of formula (II))

NMR (CD$_3$OD, external TMS)

δ=1.1-3.0 (m, 14H), 3.1-4.0 (m, 6H), 4.2-4.6 (t, H, J=5 Hz), 5.40 (s, 2H), 7.57 (s, 5H)

IR (KBr)

ν (cm$^{-1}$)=3310, 2930, 1730, 1650, 1535, 1450, 1255, 1165, 1110

TLC (chloroform:methanol:17% ammonia water=6:2.5:0.5, v/v)

Rf=0.49 ii)

16-Guanidino-7-(RS)-hydroxy-6,10-dioxo-5,9-diazahexadecanoic acid (Compound No. 24)

NMR (D$_2$O, external TMS)

δ=1.5-2.5 (m, 10H), 2.5-3.1 (m, 4H), 3.4-4.2 (m, 6H), 4.5-4.9 (t, H, J=5 Hz)

IR (KBr)

ν (cm$^{-1}$)=3310, 3170, 2930, 2860, 1715, 1645, 1540, 1435, 1170, 1110

SYNTHESIS OF COMPOUND NO. 36 i) Benzyl 16-guanidino-6-(RS)-hydroxy-5,10-dioxo-4,9-diazahexadecanoate hydrochloride (Corresponding Compound of formula (II))

NMR (CD$_3$OD, external TMS)

δ=1.2-3.0 (m, 14H), 3.1-3.9 (m, 6H), 4.0-4.4 (m, H), 5.23 (s, 2H), 7.43 (s, 5H)

IR (KBr)

ν (cm$^{-1}$)=3320, 3170, 2940, 1730, 1645, 1535, 1450, 1255, 1170

TLC (chloroform:methanol:17% ammonia water=6:2.5:0.5, v/v)

Rf=0.34 ii)

16-Guanidino-6-(RS)-hydroxy-5,10-dioxo-4,9-diazahexadecanoic acid (Compound No. 36)

NMR (D$_2$O, external TMS)

δ=1.2-3.2 (m, 14H), 3.4-4.2 (m, 6H), 4.4-4.8 (m, H)

IR (KBr)

ν (cm$^{-1}$)=3320, 2930, 2860, 1640, 1540, 1440, 1405, 1270, 1190, 1110, 1065

EXAMPLE 2

Synthesis of 16-guanidino-7-(S)-hydroxy-5,10-dioxo-4,9-diazahexadecanoic acid (S form of Compound No. 2)

a) Synthesis of benzyl 9-t-butyloxycarbonyl-7-(S)-hydroxy-5-oxo-4,9-diazanonanoate In 70 ml of dichloromethane were dissolved 1.76 g (8.02 mmols) of γ-N-t-butyloxycarbonyl-β-(S)-hydroxybutanoic acid and 1.84 g (12.02 mmols) of N-hydroxybenzotriazole. The solution was cooled with ice and 2.48 g (12.02 mmols) of N,N'-dicyclohexylcarbodiimide was added to the solution. The mixture was reacted for 15 minutes under ice cooling. Then, a solution of 2.82 g (8.02 mmols) of β-alanine benzyl ester p-toluenesulfonic acid salt and 0.89 g (8.79 mmols) of triethylamine in dichloromethane was added to the solution under ice cooling. The temperature was then reverted to room temperature and the reaction was carried out for several hours. Insoluble matters were filtered off and the filtrate was concentrated under reduced pressure. The oily residue was dissolved in 130 ml of ethyl acetate followed by washing sequentially with distilled water, 5% phosphoric acid, 5% sodium carbonate aqueous solution and then saturated sodium chloride aqueous solution. The organic layer was drived over anhydrous sodium sulfate. The supernatant was concentrated under reduced pressure to give 4.5 g of light yellow oily product. The oily product was subjected to column chromatography using Silica Gel 60 (manufactured by Merck Inc.) and development was performed with a solvent mixture of chloroform-methanol (30:1, v/v) to give 3.03 g (yield, 100%) of the oily product.

NMR (CD$_3$OD)

δ=1.47 (s, 9H), 2.1-2.5 (d, 2H, J=6 Hz), 2.4-2.8 (t, 2H, J=6 Hz), 2.9-3.3 (d, 2H, J=6 Hz), 3.2-3.7 (t, 2H, J=6 Hz), 3.8-4.3 (q, H, J=6 Hz), 5.15 (s, 2H), 7.37 (s, 5H)

TLC (chloroform:methanol=10 :1, v/v)

Rf=0.45 b) Synthesis of benzyl 8-amino-7-(S)-hydroxy-5-oxo-4-azaoctanoate hydrochloride

After 3.04 g (8.00 mmols) of benzyl 9-t-butyloxycarbonyl-7-(S)-hydroxy-5-oxo-4,9-diazanonanoate was dissolved in 20 ml of dichloromethane, 10 ml of 4 N hydrochloric acid-dioxan solution was added to the solution under ice cooling. The temperature was reverted to room temperature and the mixture was reacted for 3 hours. The reaction solution was concentrated under reduced pressure. The resulting white residue was subjected to decantation with n-hexane and ether. Concentration under reduced pressure gave 2.53 g (yield, 100%) of the oily product.

TLC (chloroform:methanol:17% ammonia water=6:2.5:0.5, v/v)

Rf=0.35 c) Synthesis of benzyl 16-guanidino-7-(S)-hydroxy-5,10-dioxo-4,9-diazahexadecanoate hydrochloride After 1.97 g (8.81 mmols) of 7-guanidinoheptanoate hydrochloride was dissolved in 40 ml of dimethylformamide, 1.22 g (10.60 mmols) of N-hydroxysuccinimide and 2.20 g (10.60 mmols) of N,N'-dicylohexylcarbodiimide were added to the solution under ice cooling. The mixture was reacted at room temperature overnight.

The precipitates were filtered off and the filtrate was used for the subsequent reaction as it was.

After 2.53 g (8.00 mmols) of the oily benzyl 8-amino-7-(S)-hydroxy-5-oxo-4-azaoctanoate hydrochloride was dissolved in 40 ml of dimethylformamide, 0.81 g (8.00 mmols) of triethylamine was added to the solution under ice cooling. Then the aforesaid solution of 7-guanidinoheptanoate hydrochloride N-hydroxysuccinimide ester in dimethylformamide was added to the mixture followed by reacting for 3 hours under ice cooling. The reaction solution was filtered and the filtrate was concentrated under reduced pressure. After decantation of the resulting oily residue twice with 100 ml of n-hexane, the system was concentrated under reduced pressure. The resulting oily product was subjected to column chromatography using Silica Gel 60 (manufactured by Merck Inc.) and development was performed with a solvent mixture of chloroform-methanol-17% ammonia water (6:2.5:0.5, v/v) to give 2.6 g (yield, 66.83%) of the oily product.

NMR (CD$_3$OD)
$\delta$ = 0.9–2.1 (m, 8H), 2.1–3.0 (m, 6H), 3.0–3.9 (m, 6H0, 3.9–4.4 (m, H), 5.23 (s, 2H), 7.46 (S, 5H)
TLC (chloroform:methanol:17% ammonia water = 6:2.5:0.5, v/v)
Rf = 0.34 d) Synthesis of 16-guanidino-7-(S)-hydroxy-5,10-dioxo4,9-diazahesadecanoic acid

After 2.6 9 (5.35 mmols) of benzyl 16-guanidino-7-(S)-hydroxy-5,10-dioxo-4,9-diazahexadecanoate was dissolved in 40 ml of methanol, 10 ml of acetic acid and 0.4 g of palladium black were added to the solution followed by catalytic reduction at 50° C. for 4 hours under normal pressure. The catalyst was filtered off and the filtrate was concentrated under reduced pressure to give 2.8 g of the oily product.

This oily product was dissolved in 40 ml of distilled water and the solution was passed through a column packed with 300 ml of CM-Sephadex ® C-25 (Na+). After eluting with distilled water, the fraction containing the desired product was collected and evaporated to dryness under reduced pressure to give 1.8 g of the dry solid. In order to remove a small amount of impurities, the resulting dry solid was dissolved in 30 ml of distilled water and the solution was passed through a column packed with 110 ml of HP-20 ® manufactured by Mitsubishi Chemical Industry Co., Ltd. By eluting with distilled water, the fraction containing the desired product was collected and concentrated under reduced pressure. The resulting oily product was dissolved in 20 ml of distilled water. Insoluble matters were filtered off and the filtrate was freeze-dried to give 1.25 g (yield, 65.10%) of the desired product.

NMR (D$_2$O, external TMS)
$\delta$ = 1.4–2.4 (m, 8H), 2.5–3.1 (m, 6H), 3.3–4.1 (m, 6H), 4.2–4.7 (m, H)
IR (KBr)
$\nu$ (cm$^{-1}$) = 3330, 2940, 2870, 1640, 1545, 1400, 1355, 1170, 1090
$[\alpha]_D^{20}$ −3.1° (c = 1.00, H$_2$O)

EXAMPLE 3

Synthesis of 16-guanidino-7-(R)-hydroxy-5,10-dioxo-4,9-diazahexadecanoic acid (R form of Compound No. 2)

The procedures were carried out in a manner similar to Example 2. Physical properties are given below.

a) Benzyl 16-guanidino-7-(R)-hydroxy-5,10-dioxo-4,9-diazanonanoate hydrochloride NMR (CD$_3$OD)
$\delta$ = 0.9–2.1 (m, 8H), 2.1–3.0 (m, 6H), 3.0–3.9 (m, 6H), 3.9–4.4 (m, H), 5.23 (s, 2H), 7.46 (s, 5H)
TLC (chloroform:methanol:17% ammonia water = 6:2.5:0.5, v/v)
Rf = 0.34

16-Guanidino-7-(R)-hydroxy-5,10-dioxo-4.9-diazahexadecanoic acid

NMR (D$_2$O, external TMS)
$\delta$ = 1.4–2.4 (m, 8H), 2.5–3.2 (m, 6H), 3.3–4.1 (m, 6H), 4.2–4.8 (m, H)
IR (KBr)
$\nu$ (cm$^{-1}$) = 3330, 2950, 2870, 1650, 1545,0 1400, 1190
$[\alpha]_D^{20}$ 1.6° (c = 1.00, H$_2$O)

What is claimed is:

1. A novel spergualin derivative represented by the general formula (I):

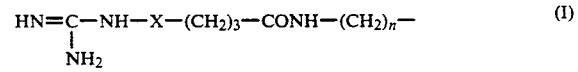

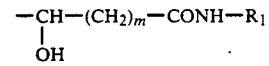

wherein X represents —(CH$_2$)$_{1\text{-}5}$—, a phenylene group, or a phenylene group substituted with a halogen atom, a lower alkyl group, or a lower alkoxy group; m represents 0, 1 or 2; n represents 1 or 2, R$_1$ represents —(CH$_2$)$_{1\text{-}3}$—COOH; and a pharmacologically acceptable salt thereof.

2. A spergualin derivative according to claim 1, wherein X is —(CH$_2$)$_3$— or —(CH$_2$)$_5$—; m is 0 or 1; n is 1; and R$_1$ is —(CH$_2$)$_2$—COOH or —(CH$_2$)$_3$—COOH.

3. A spergualin derivative according to claim 2, wherein X is —(CH$_2$)$_3$—.

4. A spergualin derivative according to claim 2, wherein steric configuration of the asymmetric carbon atom is RS form or S form.

5. A spergualin derivative represented by the formula:

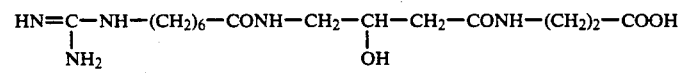

or a pharmacologically acceptable salt thereof.

6. A spergualin derivative according to claim 5, wherein steric configuration of the asymmetric carbon atom is S form.

7. A pharmaceutical composition for immunopotentiation comprising as an active ingredient a novel spergualin derivative represented by the general formula (I):

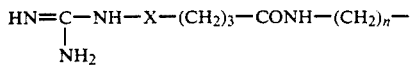(I)

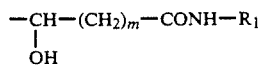

wherein X represents $-(CH_2)_{1-5}-$, a phenylene group, or a phenylene group substituted with a halogen atom, a lower alkyl group, or a lower alkoxy group, m represents 0, 1 or 2; n represents 1 or 2; and $R_1$ represents $-(CH_2)_{1-3}-COOH$; or a pharmacologically acceptable salt thereof, together with a pharmaceutically acceptable carrier.

8. A pharmaceutical composition for immunopotentiation comprising as an active ingredient a spergualin derivative represented by formula:

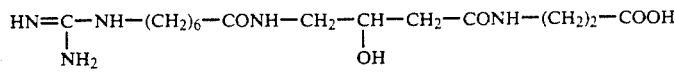

or a pharmacologically acceptable salt thereof, together with a pharmaceutical carrier.

9. A method for immunopotentiation which comprises administering an effective amount of a spergualin derivative represented by the general formula (I):

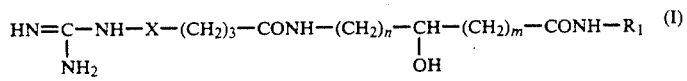 (I)

wherein X represents $-(CH_2)_{1-5}-$, a phenylene group, or a phenylene group substituted with a halogen atom, a lower alkyl group, or a lower alkoxy group, m represents 0, 1 or 2; n represents 1 or 2; and $R_1$ represents $-(CH_2)_{1-3}-COOH$; or a pharmacologically acceptable salt thereof, to a warm blooded animal having a reduced immunity.

* * * * *